US009314582B2

(12) United States Patent
Korneff et al.

(10) Patent No.: US 9,314,582 B2
(45) Date of Patent: Apr. 19, 2016

(54) HUMIDIFICATION SYSTEM

(75) Inventors: Neil Alex Korneff, Diamond Bar, CA (US); Paul David Dixon, London (GB); Christopher M. Varga, Laguna Hills, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 463 days.

(21) Appl. No.: 12/952,658

(22) Filed: Nov. 23, 2010

(65) Prior Publication Data

US 2012/0125334 A1    May 24, 2012

(51) Int. Cl.
| | | |
|---|---|---|
| *A61M 16/16* | (2006.01) | |
| *A61M 11/00* | (2006.01) | |
| *A61M 16/10* | (2006.01) | |
| A61M 16/20 | (2006.01) | |
| A61M 16/00 | (2006.01) | |
| A61M 11/04 | (2006.01) | |

(52) U.S. Cl.
CPC .............. *A61M 16/16* (2013.01); *A61M 11/005* (2013.01); *A61M 16/109* (2014.02); *A61M 16/1085* (2014.02); *A61M 16/161* (2014.02); *A61M 11/042* (2014.02); *A61M 16/162* (2013.01); *A61M 16/20* (2013.01); *A61M 2016/0039* (2013.01); *A61M 2205/3368* (2013.01)

(58) Field of Classification Search
CPC .............. A61M 16/16; A61M 16/161; A61M 16/1085; A61M 16/109; A61M 11/005; A61M 16/162; A61M 16/20; A61M 2205/3368; A61M 2016/0039; A61M 11/04; A61M 11/041; A61M 11/042; A61M 16/0108; A61M 16/201; A61M 16/202; A61M 2205/362; A62B 9/00; A62B 9/003
USPC ............. 128/203.26, 203.17, 201.13, 203.16, 128/203.27, 204.12, 204.14, 204.17, 206.27
See application file for complete search history.

(56) References Cited

U.S. PATENT DOCUMENTS

| | | | | |
|---|---|---|---|---|
| 4,159,803 | A | | 7/1979 | Cameto et al. |
| 4,829,998 | A | * | 5/1989 | Jackson .................... 128/203.12 |
| 5,148,801 | A | * | 9/1992 | Douwens et al. ........ 128/203.16 |
| 5,445,143 | A | | 8/1995 | Sims |
| 5,518,179 | A | | 5/1996 | Humberstone et al. |
| 5,890,490 | A | | 4/1999 | Aylsworth et al. |
| 6,078,730 | A | | 6/2000 | Huddart et al. |
| 6,095,505 | A | * | 8/2000 | Miller ........................... 261/130 |
| 6,102,037 | A | * | 8/2000 | Koch ......................... 128/203.26 |

(Continued)

FOREIGN PATENT DOCUMENTS

| | | |
|---|---|---|
| DE | 43 12 793 A1 | 10/1994 |
| WO | WO 2009022004 A2 * | 2/2009 |
| WO | WO 2009/146484 A1 | 12/2009 |

*Primary Examiner* — Tan-Uyen (Jackie) T Ho
*Assistant Examiner* — Mark K Han
(74) *Attorney, Agent, or Firm* — Arent Fox LLP

(57) ABSTRACT

The present invention provides a method for reducing condensed humidifying agent in a humidification system by pulsing a delivery of humidifying agent into a respiratory circuit. During a non-pulsed interval, gas flowing through the respiratory circuit will evaporate the condensed humidifying agent present in the respiratory circuit. The present invention also provides a method and apparatus for delivering humidified gas to a patient, wherein the delivery avoids the problems associated with a stationary water humidifier. In the method, the delivery of humidifying agent is precisely controlled to deliver a flow of humidifying agent to a volume of gas.

16 Claims, 4 Drawing Sheets

(56) References Cited

U.S. PATENT DOCUMENTS

| | | | |
|---|---|---|---|
| 6,859,617 B2* | 2/2005 | Goodsel et al. | 392/478 |
| 6,918,389 B2* | 7/2005 | Seakins et al. | 128/203.27 |
| 7,073,500 B2* | 7/2006 | Kates | 128/203.16 |
| 7,146,979 B2 | 12/2006 | Seakins et al. | |
| 7,267,121 B2 | 9/2007 | Ivri | |
| 7,694,675 B2 | 4/2010 | Koch et al. | |
| 2005/0139221 A1* | 6/2005 | Duncan | 128/207.18 |
| 2007/0051368 A1* | 3/2007 | Seakins et al. | 128/203.17 |
| 2007/0277825 A1* | 12/2007 | Bordewick et al. | 128/204.23 |
| 2008/0302362 A1* | 12/2008 | Kwok | 128/203.16 |
| 2009/0224064 A1 | 9/2009 | Brodbeck et al. | |
| 2009/0241948 A1 | 10/2009 | Clancy et al. | |
| 2009/0267242 A1* | 10/2009 | Nichols et al. | 261/4 |
| 2010/0242956 A1* | 9/2010 | Yamada et al. | 128/200.23 |
| 2012/0017904 A1* | 1/2012 | Ratto et al. | 128/203.26 |

\* cited by examiner

HUMIDIFICATION SYSTEM

FIELD OF THE INVENTION

Aspects of the present invention relate to humidification systems which provide humidified gas to a patient.

BACKGROUND OF THE INVENTION

Humidification systems have long been used to treat patients in need of respiratory assistance. A typical humidification system generally includes a source of gas, a source of water vapor, and a delivery system. In the typical humidification systems, the water vapor is first produced by heating a stationary body of water contained in a humidifying chamber. Then, the water vapor mixes with gases passing through the humidifying chamber, thereby humidifying the gas. However, heating the body of water to a point sufficient to produce water vapor can take a significant amount of time, depending on the amount of water contained in the chamber. In the stationary water humidifier, the humidifying chamber containing the water is arranged so that the water vapor mixes with the gas flowing through the humidifying chamber, thereby humidifying the gas. Furthermore, because the stationary water is heated, when the gas passes over the heated water, the gas is also heated. Thus, a heating step occurs simultaneously with the humidifying step. The humidified gas then proceeds through a respiratory circuit, which directs the humidified gas to a patient. U.S. Pat. No. 5,445,143 discloses such a system.

It is known to implement a stationary water humidifier in a humidifying system having parallel gas flow paths. U.S. Pat. No. 7,146,979 discloses such a system. In particular, U.S. Pat. No. 7,146,979 discloses a humidification system having a valve for splitting a gas into two different paths, wherein one path is humidified while the other is heated by a heater. The system is capable of adjusting the valve to control the relative humidity of the gas being delivered to the patient. However, operating the system in this manner requires implementing sensors for determining relative and absolute humidity of the gas.

Other humidification systems may meter a flow of water to an evaporator. U.S. Pat. No. 6,102,037 describes such a system. The system disclosed in U.S. Pat. No. 6,102,037 provides water vapor with a temperature above 134° C., which heats the respiratory gas. Another humidification system has been disclosed that avoids pumping water and reduces the time required to heat the water by using a capillary system. For example, U.S. Pat. No. 7,694,675 uses a low porosity sintered glass or ceramic to draw water to and through an evaporator tube, where the water is evaporated into a gas.

Regardless of the type of humidifier used, conventional humidifying systems implement a respiratory circuit to provide a flow path from the humidified gas to the patient. Many of the known humidification systems are capable of delivering over 100 Watts to evaporate the water. Therefore, it is preferable to locate the evaporating components away from the patient to simplify system design and minimize patient risk. Furthermore, it would not be comfortable for the patient to have bulky equipment located directly by the patient's face. It is also important to ensure the gas flow being received by the patient arrives at a safe temperature, which is capable of being measured and controlled. By providing a respiratory circuit extending from the humidifier to the patient, the above problems are avoided. However, using a respiratory circuit to deliver the humidified gas creates additional problems.

A significant problem that occurs when using a respiratory circuit to deliver humidified gas is the formation of condensation in the respiratory circuit. Condensation, or "rainout," occurs due to the temperature gradient existing between the respiratory circuit and the external temperature of the patient's room. The ambient room temperature is generally lower than the temperature of the gases inside the respiratory circuit because the patient's room is usually maintained at a comfortable level for the patient. As humidified gas flow passes within the relatively colder walls of a respiratory circuit, a certain amount of water vapor will condense along the walls of the respiratory circuit. After too much condensation builds up, a practitioner must manually remove the condensation from the respiratory circuit because it is dangerous for a patient to accidentally inhale liquid. The manual removal of condensation requires taking apart the respiratory circuit or replacing the respiratory circuit, which can take a substantial amount of time. Taking down the circuit to remove condensation breaks the continuity of delivering humidified gas to the patient. Furthermore opening the circuit to remove condensation causes a loss of respiratory pressure support and may result in alelactasis or respiratory distress.

Several of the known humidification systems attempt to solve the problem by providing heated elements within the respiratory circuit itself. By selectively heating the heated elements, the operator maintains a temperature of the heated walls to maintain the temperature of the gas above the dewpoint, thereby potentially reducing condensation. Such a system is disclosed in U.S. Pat. No. 7,146,979. However, as discussed in U.S. Pat. No. 6,078,730, in such a system, the temperature is highest close to the wire, but low on the wall across from the heater, thereby allowing condensation to occur. To improve on this system, U.S. Pat. No. 6,078,730 discloses an alternative humidification system that includes a heater wire sitting against or adjacent to an internal wall of a respiratory conduit. Furthermore, DE 4312793 discloses a humidification system having a heater provided in a respiratory circuit. However, these systems require additional heated elements and controls to heat the respiratory circuit walls and the gas to reduce the condensation.

Thus, there is a need in the art for a simple method for reducing condensation in a respiratory circuit.

SUMMARY OF THE INVENTION

The present invention provides a method of reducing condensed humidifying agent in a humidification system, the method includes providing a humidification system having a respiratory circuit for delivering a volume of gas to a patient and a humidifier portion for delivering a humidifying agent to the volume of gas, pulsing a delivery of the humidifying agent to the volume of gas at a pulsed interval via the humidifier portion, heating the volume of gas, and vaporizing, during a non-pulsed interval, condensed humidifying agent present in the respiratory circuit to reduce the condensed humidifying agent present in the humidification system.

The present invention also provides a method of delivering a humidified volume of gas to a patient, the method including providing a humidification system having a respiratory circuit for delivering the volume of gas to a patient and a humidifier portion for delivering a humidifying agent to the volume of gas, providing the humidifying agent at a controlled flow rate to the humidifier portion via a humidifying agent input line, vaporizing the humidifying agent via a heated element, delivering the humidifying agent to the volume of gas, thereby humidifying the volume of gas, heating the gas flow, and delivering the humidified volume of gas to the patient via the respiratory circuit.

The present invention also provides a humidification system for carrying out the method of reducing condensed humidifying agent and the method of delivering humidified gas.

The above and still other advantages of the invention will be apparent from the detailed description and drawings. What follows are one or more preferred embodiments of the present invention.

DETAILED DESCRIPTION OF THE INVENTION

The present invention provides a method of removing condensed humidifying agent from a humidification system, a method of delivering humidifying gas to a patient, and a humidification system for performing the methods. It is to be understood that the term gas is intended to include any gas suitable for use with the following disclosure. For example, the gas may comprise oxygen, ambient air, or any other breathable gas. The method of removing condensed humidifying agent includes pulsing the delivery of a humidifying agent to a heated volume of gas as the volume of gas travels towards the patient and evaporating the condensed humidifying agent during a non-pulsed interval. The method of delivering humidified gas to the patient includes delivering a controlled amount of humidifying agent to a humidifier portion. Thus, the present invention effectively and easily allows a practitioner to reduce condensation present in a humidification system by removing condensation. Furthermore, the present invention also provides an alternative to a humidifier having a stationary water chamber.

Figure 1:
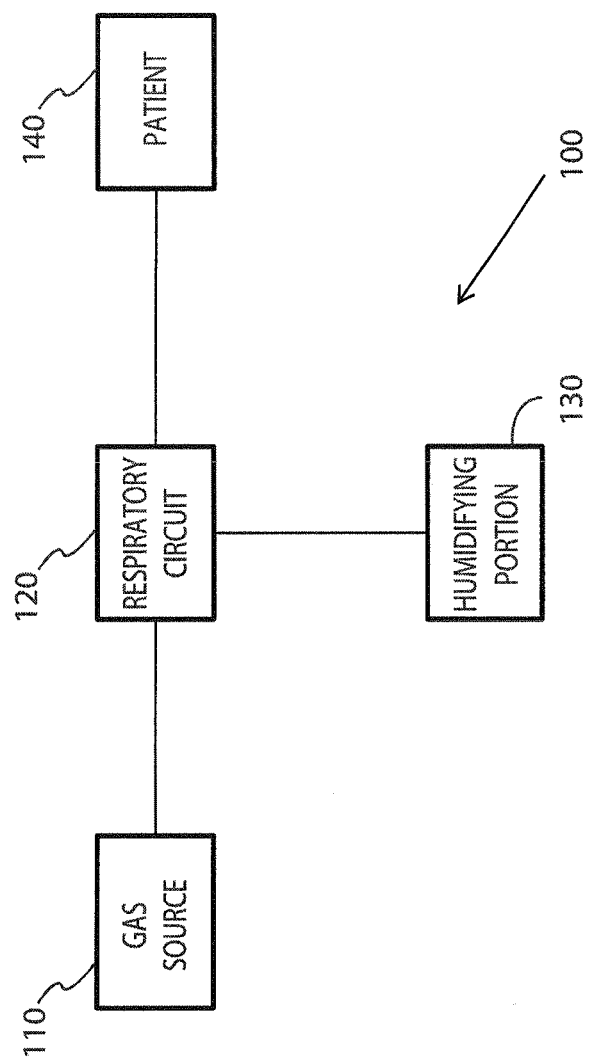
FIG. 1 is schematic overview of a humidification system.

FIG. 1 illustrates a schematic overview of an exemplary humidification system in which the inventive methods may be implemented. The humidification system 100 includes a gas source 110 in communication with a respiratory circuit 120 and a humidifying portion 130. The humidifying portion 130 is also in communication with the respiratory circuit 120 at a point downstream of the gas source 110. The gas source 110 may be any suitable device that provides a flow of gas to be provided to a patient, such as a lung ventilator. The humidifying portion 130 includes a device capable of providing a humidifying agent to the gas flow as the gas flow travels through the respiratory circuit 120. Exemplary aspects of the humidifying portion 130 are provided in more detail herein. The respiratory circuit 120 delivers the humidified gas having humidifying agent to a patient 140. Throughout this disclosure, the term "humidifying agent" is intended to encompass any agent capable of humidifying the flow of gas. It should also be understood that the humidifying agent may be any agent that may be delivered to a patient via an inhaled volume of gas, including aerosolized or vaporized medicine. In one aspect of the invention the humidifying agent comprises water. The respiratory circuit 120 also provides an exhaust path for gas being exhaled by the patient.

In the exemplary aspects described herein, the humidifying portion 130 vaporizes the humidifying agent and delivers the vaporized humidifying agent to the volume of gas. The volume of gas provided to the respiratory circuit 120 is generally dryer and colder relative to the later humidified state when the gas is first provided from the gas source 110. The gas flow is heated at one or more of the following points in flow path: before passing through the humidifying portion 130, while passing through the humidifying portion, and after exiting the humidifying portion 130. Thus, when the humidifying agent is delivered to the volume of gas via the humidifying portion 130, the volume of gas becomes more humid, while the heating step ensures the humidifying agent is in a vapor state, thereby making the gas safe for breathing. The respiratory circuit 120 is also in communication with the patient 140 at a point downstream of the humidifying portion 130. Thus, after the humidifying agent is delivered to the volume of gas, the humidified volume of gas reaches the patient 140 and is inhaled by the patient 140. The patient then exhales through an exhaust portion of the respiratory circuit 120. The exhaust portion may lead back to the gas source 110.

In an exemplary aspect of the present invention, the humidifying portion 130 is operated to pulse the delivery of humidifying agent to a volume of gas flowing through the respiratory circuit 120. The gas source 110 is configured to provide a volume of gas corresponding to a patient's normal breathing volume. More specifically, the humidifying portion 130 is operated to quickly increase the delivery of humidifying agent to the volume of gas that is being delivered to the patient 140. During patient exhalation, the gas source 110 provides a second volume of gas, alternatively referred hereinafter to as a bias volume. At a time when it is desirable to remove condensation from the respiratory circuit 120, i.e., when the bias volume of gas is being delivered, the humidifying portion 130 is operated so that less humidifying agent is delivered to the bias volume of gas as compared to the pulsed delivery of humidifying agent to the inhaled volume of gas. Because the bias volume of gas has less humidifying agent as it passes through the respiratory circuit 120, the bias volume of gas will vaporize condensed humidifying agent present in the respiratory circuit 120. Thus, in the non-pulsed interval, the flow of the bias volume of gas effectively removes condensed humidifying agent from the respiratory circuit 120. As will be described in more detail herein, in one aspect the pulse may be provided by directing a volume of gas toward the humidifying portion 130, while in another aspect the pulse may be provided by controlling the rate of flow of humidifying agent into the humidifying portion 130.

In an aspect of the present invention, the timing of the pulse may be set according to the breathing pattern of the patient 140. For example, because it is desirable for the patient to receive the humidified gas during inhalation, the humidifying portion 130 may be operated to pulse the delivery of humidifying agent to a volume of gas at the start of inhalation or immediately following patient exhalation. Likewise, it is not desirable for the patient 140 to inhale a non-humidified gas stream. Therefore, in an aspect of the present invention the humidifying portion 130 may be operated to provide humidifying agent to a bias volume of gas in the non-pulsed state during patient exhalation or immediately after patient inhalation. By delivering the pulse in the above-described manner, the patient 140 will preferentially receive humidified gas when inhaling and the respiratory circuit 120 may be cleared of condensation at other times.

Additionally, the timing of the pulse may be set so that the volume of gas containing a pulsed amount of humidifying agent is present in some part of the respiratory circuit 120 at the same time a bias volume of gas containing a non-pulsed amount of humidifying agent is present in another part of the respiratory circuit 120. For example, a bias gas may be delivered to the respiratory circuit 120 from the gas source 110, to which a non-pulsed amount of humidifying agent is delivered. Immediately following, while the non-pulsed bias volume is traveling through respiratory circuit and evaporating condensation, a volume of gas to which the pulsed amount of humidifying agent is delivered, is provided to the respiratory circuit. Accordingly, the condensation is being evaporated while the volume of gas receiving a pulsed amount of humidifying agent is traveling through the respiratory circuit. It is also within the scope of the invention that under certain circumstances the bias volume receiving the non-pulsed delivery of humidifying agent may be delivered the patient. The non-pulsed bias volume may be delivered to the patient when the amount of condensation present in the respiratory circuit 120 is great enough that the bias volume ultimately ends up being adequately humidified as the gas travels through the respiratory circuit 120.

The method of delivering humidified gas to a patient 140 also uses the above-described components of the humidifying system 100. The method provides a manner of delivering a controlled amount of humidifying agent to the gas stream, thereby avoiding the problems associated with a stationary water humidifier, while allowing precise control of the amount of humidifying agent delivered to the dry gas. As with the method of reducing condensed humidifying agent, in the method of delivering humidified gas, the volume of gas flowing from the gas source 110 is heated to the proper temperature to ensure the humidifying agent is vaporized before reaching the patient. The heating step may be performed as described above, i.e. before, after, or simultaneous with the humidifying step. Also as described above, the volume of gas flows to the humidifying portion 130 of the humidification system 100 where the humidification of the volume of gas occurs. In an exemplary aspect of the present invention, instead of including a stationary water humidifier, the humidifying portion 130 includes a flow controller that controls delivery of the humidifying agent to a heated element. The flow controller may be operated and controlled to provide a particular flow of humidifying agent to the humidifying portion 130. More specifically, by optimizing the flow of humidifying agent delivered to the humidifying portion 130, the amount of humidifying agent delivered to the volume of gas may be precisely controlled. As discussed in more detail herein, the other variables may be controlled, such as, but not limited to, fresh gas flow rate and heated element temperature. Furthermore, by delivering humidifying agent to a heated element, the above-described disadvantages of the stationary water humidifier are avoided. In particular, as discussed in more detail herein, by delivering humidifying agent, the heating step and the humidifying step will not occur simultaneously, thereby allowing more flexibility in controlling the system.

Figure 2:
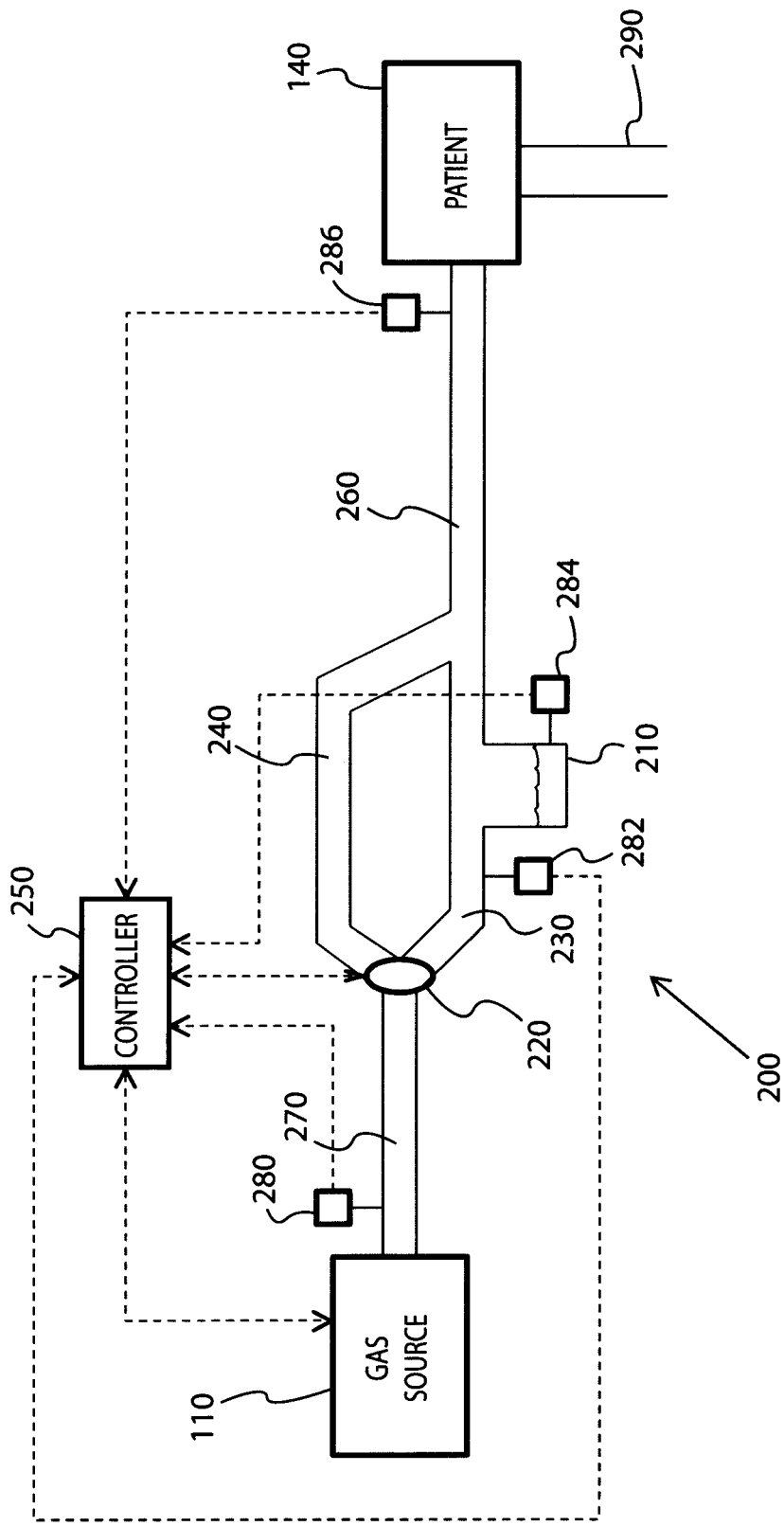
FIG. 2 is a schematic view of a first aspect of the humidification system of FIG. 1.

Several exemplary aspects of the humidifying portion will now be described. FIG. 2 illustrates a first exemplary aspect of the humidifying portion 200. The humidifying portion 200 includes a stationary humidifying agent humidifier 210 and a diverter 220 for diverting a volume of gas. The diverter 220 may include any apparatus capable of partially or entirely diverting the flow of a volume of gas traveling from a gas source 110, through a gas inlet line 270, into a humidifying flow path 230 and a diverted flow path 240. As shown in FIG. 2, in an exemplary aspect, the diverter 220 is a valve. The valve may be a simple toggle valve that directs the entire flow to the humidifying flow path 230 and the diverted flow path 240, or it may allow for a particular ratio split between the humidifying flow path 230 and the diverted flow path 240. For example, the diverter 220 may be capable of splitting the gas flow from anywhere between 100% of the flow in one of the flow paths and 0% in the other to 50% in both paths. In order to facilitate precise control of the diverter 220 a controller 250 may be coupled to the diverter 220.

As described above, when allowing the volume of gas to travel through the humidifying flow path 230, the volume of gas will pass through a chamber of heated stationary humidifying agent 210. As the volume of gas passes through the chamber, the volume of gas will absorb humidifying agent vapor and will be heated. For the reasons described above, after the humidified gas exits the humidifying portion 200, condensation may likely form in a discharge line 260 that is positioned downstream of the humidifying portion 200. In the case where at least some volume of gas passes through the humidifying flow path 230, in addition to the heating of the gas as it passes through the chamber of heated stationary water, the volume of gas may be heated upstream in the gas inlet line 270 and/or downstream in the discharge line 260. In the case where at least some volume of gas is passing through the diverted flow path 240, the gas may additionally be heated in the diverted flow path 240. The gas inlet line 270, the diverted flow path 240, and the discharge line 260 may each include a heating element (not shown), such as a heating wire, to facilitate the additional heating. The heating elements may be used to ensure that the humidifying agent present in the volume of gas remains in a vapor state upon delivery to the patient. The heating element in the diverted flow path 240 may be used to increase the temperature of the volume of gas passing through the diverted flow path 240, thereby facilitating removal of condensation from the discharge line 260. Furthermore, when heating is carried out in the discharge line 260, the heating step may be used in conjunction with the pulsing method to further reduce condensation.

To remove the condensation from the discharge line 260, the diverter 220 may be actuated to divert the gas flow between the diverted flow path 240 and the humidifying flow path 230 in pulsed intervals. In the simplest aspect, when humidified gas is desirable, the controller 250 can actuate the diverter 220 to immediately direct all of a volume of gas through the humidifying flow path 230. Because the valve was previously directing all of a volume of gas through the diverted flow path 240, the amount of humidifying agent delivered to the volume of gas is increased, as compared to the previous volume of gas passing through the system. After the humidified gas has been delivered to the patient 140, and it becomes desirable to remove any condensation that has formed in the discharge line 260, the controller 250 can immediately actuate the diverter 220 to direct all of the volume of gas through the diverted flow path 240. Because all the gas is being directed through the diverted flow path 240, the amount of humidifying agent delivered to the volume of gas is decreased, as compared to the previous volume of gas passing through the system. Thus, by switching the diverter 220 between the two paths, the delivery of humidifying agent to the gas flow is pulsed. Furthermore, in another aspect, the above-described concept can be applied to any degree of flow splitting. For example, during the pulsing step a volume gas may be divided between the humidifying flow path 230 and the diverted flow path 240 such that 25% of the volume of gas passes through the diverted flow path 240 and 75% of the volume of gas passes through the humidifying flow path 230. In such a case the delivery of humidifying agent to the total volume of gas is being pulsed as compared to the opposite split (i.e. 25% of the volume passing through the humidifying flow path 230 and 75% passing through the diverted flow path 240). The above-described ratios are merely exemplary, and it is within the scope of the invention that any ratio of split may be used, as long as the amount of humidifying agent delivered to the volume of gas is increased (i.e. pulsed) as compared to a volume of gas (i.e. a bias volume) that is intended to remove condensation.

As shown in FIG. 2, it is desirable for the diverted flow path 240 to rejoin the discharge line 260 near the humidifying portion 200 so that the dry gas will pass through a majority of the discharge line 260, thereby maximizing the vaporization of condensed humidifying agent. Furthermore, the controller 250 may be configured to actuate the diverter 220 in accordance with the patient's inhalation and exhalation to optimize the delivery of humidified gas and the removal of condensed humidifying agent present in the discharge line 260. In an aspect of the present invention, the operation of the diverter 220 and the introduction of gas from the gas source 110 may be timed so that a volume of gas passes through the humidifier portion 200 at the same time that a bias volume of gas passes through an expiratory limb 290. As described above, due to the volume capacity of the respiratory circuit, the timing of delivery of a bias volume of gas or a volume of gas to be humidified may be set such that one of the gas volumes immediately follows the other while the first volume (whether bias or humidified) is still in the circuit. For example, while the bias volume of gas is clearing out condensation in the discharge line 260 or in the expiratory limb 290, the volume of gas to be humidified may be simultaneously entering the humidifying portion.

The controller 250 may communicate with a variety of feedback sensors 280, 282, 284, 286 to provide optimal timing of the delivery of pulsed humidifying agent to a volume of gas. In particular, sensor 280 may detect a flow rate of gas, sensor 282 may detect a temperature and flow rate of gas passing through the humidifying flow path 230, sensor 284 may detect the humidifying agent water level, temperature, and number of times the chamber has been refilled with humidifying agent, and sensor 286 may detect the temperature of the gas passing through the discharge line 260. In some aspects, the gas source 110 and the controller 250 may be preconfigured to communicate with each other such that the controller 250 receives timing/breathing pattern information from the gas source 110, such as when the gas source is a lung ventilator. When the controller 250 and gas source 110 communicate in this manner, it is not necessary to use the flow sensor 280. However, when controller 250 and the gas source 110 are not preconfigured to communicate with each other, the flow sensor 280 is necessary to control the system. Notably, in the aspect of FIG. 2, it is not necessary that any of the sensors detect relative or absolute humidity when supplying humidifying agent to a volume of gas because the pulsing of the humidifying only occurs for a brief moment. However, it is also within the scope of the invention that the sensors could detect relative and absolute humidity to assist in optimizing the delivery of humidified gas.

Figure 3:
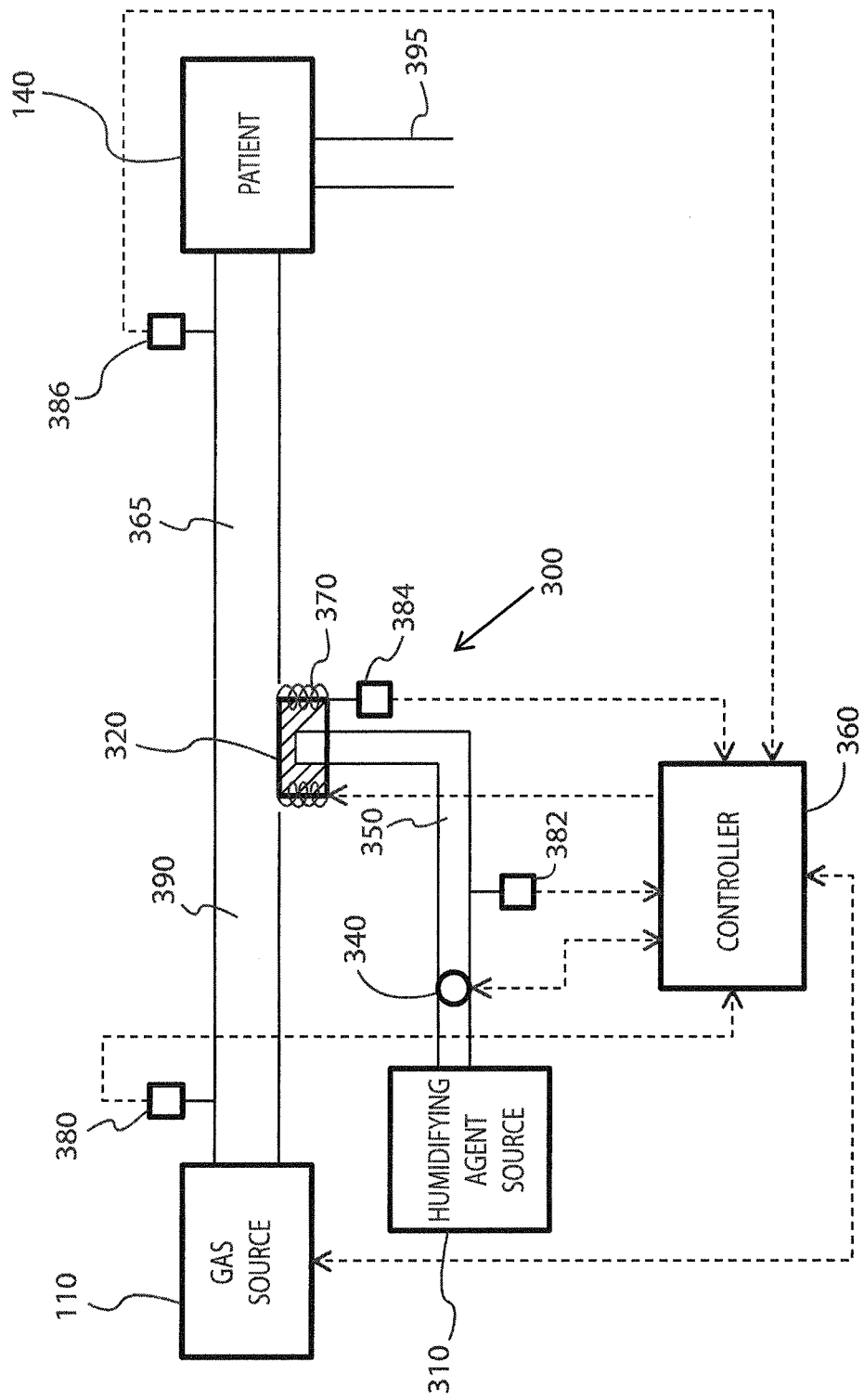
FIG. 3 is a schematic view of a second aspect of the humidification system of FIG. 1.
Figure 4:
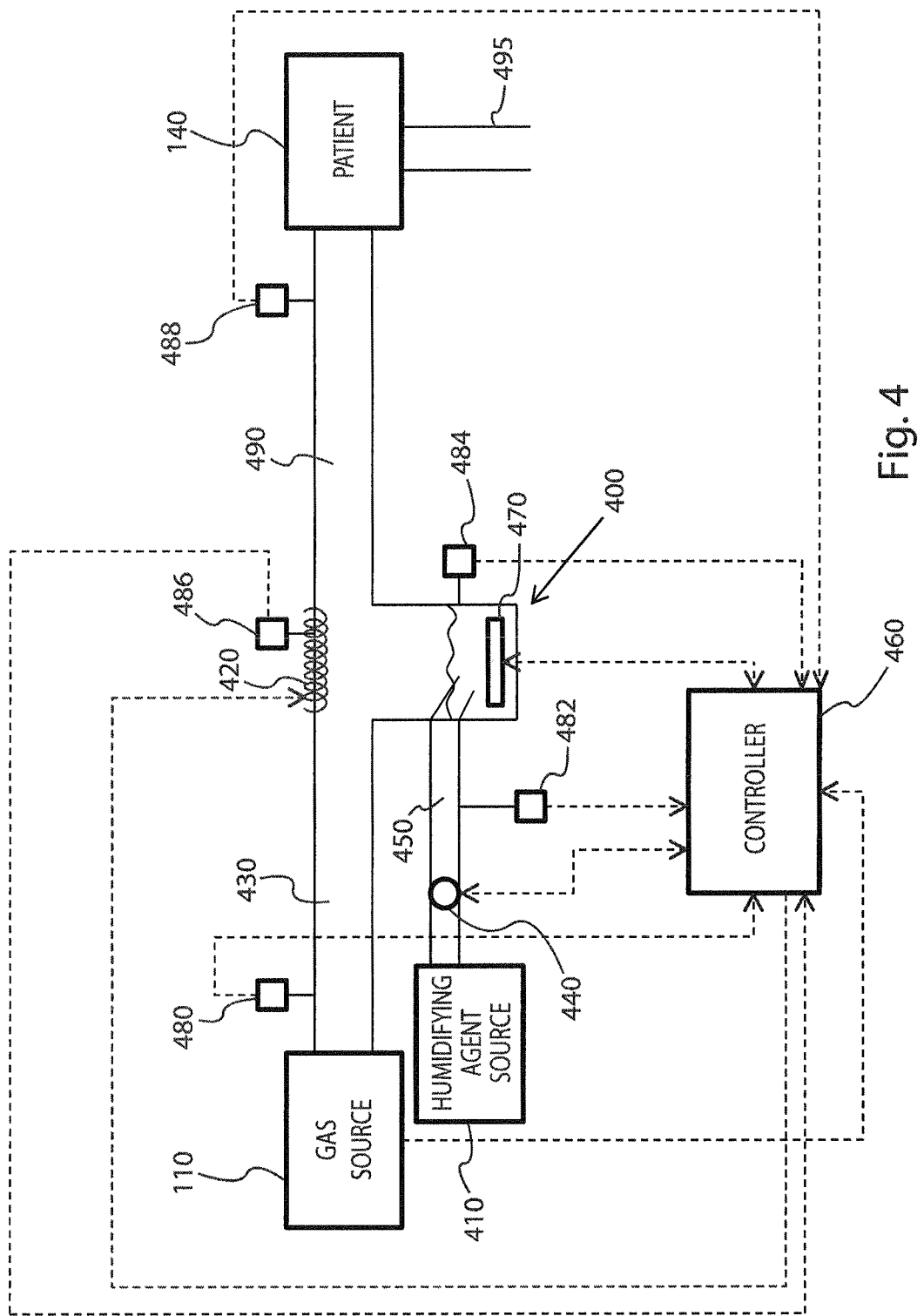
FIG. 4 is a schematic view of a third aspect of the humidification system of FIG. 1.

FIGS. 3 and 4 illustrate additional aspects of the humidifying portion. Unlike the aspect of FIG. 2, the aspects of FIGS. 3 and 4 do not include a stationary humidifying agent humidifier or a diverter. Rather, the humidifying portion 300, 400 achieves the pulsing step through controlling a flow rate of humidifying agent, thereby controlling the amount of humidifying agent that reaches the volume of gas.

In the aspect of FIG. 3, as with the aspect of FIG. 2, gas travels from the gas source 110 through a gas inlet line 390, through a humidifying portion 300, through a discharge line 365, and to a patient 140. As with the aspect of FIG. 2, the gas may be heated upstream of the humidifying portion 300 in the gas inlet line 390 (heater not shown), in the humidifying portion 300, or downstream of the humidifying portion in the discharge line 365 (heater not shown). As discussed above, maintaining the gas at a proper temperature ensures that the humidifying agent remains in a vapor state upon reaching the patient. In the aspect of FIG. 3, however, in place of a stationary humidifying agent humidifier, the humidifying portion 300 includes a heated element 320 in communication with a humidifying agent inlet line 350. In the exemplary aspect illustrated in FIG. 3, the humidifying agent inlet line 350 includes a flow controller, such as, a pump 340 for pumping the humidifying agent from a humidifying agent source 310 to the heated element 320. It is also within the scope of the invention, however, that the pump may be replaced with any suitable metering apparatus, such as gravity feeding in conjunction with a valve. Therefore, it is to be understood that all references to a "pump" or "pumping" includes any suitable metering device.

The heated element 320 is maintained at a temperature sufficient to vaporize the humidifying agent as soon as the humidifying agent comes into contact with the heated element 320. The heat from the heated element may be sufficient to heat the gas to the necessary temperature, in which case upstream and downstream heaters would not be necessary. The heated element 320 may be made of any material that is suitable of achieving this function. In an exemplary aspect, the heated element 320 may comprise a porous mass of thermally conductive material. More specifically, the heated element 320 may comprise a thermally conductive fiber wool or sintered particulate mass manufactured from, for example, copper or stainless steel. The heated element 320 may be enclosed within a heater coupling 370 to maintain the temperature of the heated element 320.

In operation, unlike the aspect of FIG. 2, in the aspect of FIG. 3, the gas flow will always pass through the humidifying portion 300. In the aspect of FIG. 3, the pulsing step is achieved by controlling the flow rate of the humidifying agent via the pump 340 or another suitable metering apparatus. When it is desirable to have humidifying agent delivered to the gas inlet line 390, the pump 340 or metering device will deliver humidifying agent directly onto the heated element 320. Upon contacting the heated element 320 the humidifying agent will vaporize and enter the gas inlet line 390. When it is desirable to have a dry volume of gas (i.e. a bias volume of gas) sent through the respiratory circuit, the pump 340 will be stopped and the humidifying agent will no longer contact the heated element 320, thereby preventing the flow of humidifying agent into the gas inlet line 390. When it is desirable to again provide humidified gas to the patient, the pump 340 may be restarted, thereby creating a pulsed delivery of humidifying agent. Furthermore, similar to the ratio split of the diverter in the aspect of FIG. 2, the rate of pumping or metering humidifying agent may be increased to produce the pulsed delivery, rather than turning the pump 340 on or off. For example, when it is desirable to provide humidifying agent to the gas inlet line 390, the pumping rate may be immediately increased to provide an increase in delivery of humidifying agent, after which the pump 340 will immediately return to the previous or lower flow rate. Thus, the delivery of humidifying agent is pulsed.

As with the aspect of FIG. 2, the pulse and delivery of a volume of gas may be timed with patient inhalation while the non-pulsed period is timed with patient exhalation. Thus, the aspect of FIG. 3 also reduces condensed humidifying agent present in the discharge line 365 that is downstream of the humidifying portion 300 when the dry bias volume of gas passes through the discharge line 365 during the non-pulsed operation. Additionally, as with the aspect of FIG. 2, the timing of the delivery of the volume of gas and pulse operation may be set so that a dry volume of gas is passing through the discharge line 365 or expiratory limb 395 at the same time a volume of gas to be humidified is passing through the humidifying portion 300.

Furthermore, a controller 360 and sensors 380, 382, 384, 386 may be implemented in a similar manner as in the aspect of FIG. 2 in order to detect relevant system parameters and control the flow of gas and humidifying agent in an optimal manner. In particular, the pump 340 may be controlled by a controller 360 to allow for precise timing of the pulses and the gas source 110 may be controlled to time the delivery of a volume of gas. Sensor 380 may be implemented to detect temperature and flow rate of the gas being delivered from the gas source 110, sensor 382 may be implemented to detect flow rate, temperature, and pressure of the humidifying agent being delivered to the heating element, sensor 384 may be implemented to detect the temperature of the heating element 320, and sensor 386 may be implemented to detect the gas flow rate, gas temperature, relative humidity, and absolute humidity in the discharge line 365. The sensor 384 may comprise a thermocouple coupled with the heated element 320. The controller 360 may use some or all of the data detected from the various sensors to provide optimal control of any of the controllable parameters such as volume and rate of gas being delivered from the gas source, flow rate of humidifying agent to the heated element, and temperature of the heated element.

The aspect of FIG. 4 illustrates a second alternative to the stationary humidifying agent humidifier of FIG. 2. Like the aspect of FIG. 3, the aspect of FIG. 4 provides a pulsed delivery of humidifying agent without diverting the volume of gas delivered to the system. As with the above aspects, gas travels from the gas source 110 through a gas inlet line 430, through a humidifying portion 400, through a discharge line 490, and to a patient 140. As with the aspect of FIGS. 2 and 3, the gas may be heated upstream of the humidifying portion 400 in the gas inlet line 430 (not shown), in the humidifying portion 400, or downstream of the humidifying portion in the discharge line 490 (not shown). As discussed above, maintaining the gas at a proper temperature ensures that the humidifying agent remains in a vapor state upon reaching the patient. As illustrated in FIG. 4, the supply of humidifying agent to the humidifying portion 400 is similar to that in the aspect of FIG. 3. A humidifying agent source 410 stores humidifying agent that is pumped through a humidifying agent inlet line 450 via a pump 440. The humidifying agent is pumped to the humidifying portion 400. It is also within the scope of the invention, however, that the pump may be replaced with any suitable metering apparatus, such as gravity feeding in conjunction with a valve.

In the aspect of FIG. 4, the humidifying portion 400 includes a droplet generating device 470. The droplet generating device 470 may be any suitable apparatus that will produce fine droplets of humidifying agent. In an exemplary aspect of the present invention, the droplet generating device 470 comprises an ultrasonic vibrating plate. The plate vibrates at an ultrasonic frequency such that when the humidifying agent contacts the plate, the fluid is nebulized into very fine droplets. The nebulizing step also forces the droplets towards the flow of heated gas that is traveling toward the patient 140 through the gas inlet line 430. Any droplet generating device suitable for producing fine droplets may be implemented in the aspect of FIG. 4. For example, U.S. Pat. No. 4,159,803 discloses ultrasonic aerosol generation via an ultrasonic nebulizer, the disclosure of which is hereby incorporated by reference. U.S. Pat. No. 5,518,179 discloses ultrasonic aerosol generation using a plate with a plurality of small perforations, induced to vibrate at ultrasonic frequencies such as to eject droplets of liquid from a liquid reservoir on one face to a gas volume on the opposing face, the disclosure of which is hereby incorporated by reference. Additionally, U.S. Pat. No. 7,267,121 discloses producing an aerosol via a nebulizer into a gas flow, the disclosure of which is hereby incorporated by reference. The aerosol generating devices disclosed by these references may be implemented as the droplet generating device 470.

Unlike the above-described aspects, the humidifying portion 400 does not convert the humidifying agent to vapor before it reaches the volume of gas passing through the humidifying portion 400. Rather, the fine droplets, which are still in a liquid state, are delivered to the gas inlet line 430 and are vaporized within the volume of gas. The fine droplets are vaporized when the droplets enter the gas inlet line 430 when the entry point into the gas inlet line 430 includes a heated element 420, as shown in the exemplary aspect of FIG. 4. The heated element 420 may comprise any suitable space heating device, such as a heating coil. Because the droplets are very fine as a result of the ultrasonic nebulization, the droplets will vaporize quickly upon entering the area heated by the heating element 420. Thus, as the heated gas stream passes through the humidifying portion 400, the dry gas will become humidified from the evaporated fine droplets. The heating element 420 may be sufficient to heat the volume of gas to the necessary temperature, in which case additional heaters upstream or downstream of the humidifying portion 400 would not be necessary. However, because the humidifying portion 400 injects humidifying agent droplets separately from the heating step, the heating step may be completely decoupled from the humidifying portion 400. In other words, in another aspect, the heating element 420 need not be present at the point where the droplets enter the gas stream, but instead may be present in the gas inlet line 430 upstream of the humidifying portion or in the discharge line 490 downstream of the humidifying portion. In the case where the heating is performed in the gas inlet line 430, the gas must be heated enough to evaporate the humidifying agent droplets.

The pulsing step of the aspect of FIG. 4 is analogous to the pulsing step described above with respect to the aspect of FIG. 3. When it is desirable to provide humidified gas to the patient 140, the amount of humidifying agent being delivered to the humidifying portion 400 will be immediately increased. Simultaneously, the droplet generating device 470 will be actuated. Thus, a rapid increase, or pulse, of humidifying agent droplets will be delivered to a volume of gas traveling through the gas inlet line 430. Likewise, when it is desirable to reduce condensed humidifying agent present in the discharge line 490, the delivering of humidifying agent to the humidifying portion 400 and/or the actuation of the droplet generating device 470 may be reduced or stopped. Thus, the amount of humidifying agent delivered to the volume of gas traveling through the gas inlet line 430 will be quickly reduced, thereby allowing a relatively dry volume of gas to continue through the discharge line 490. As with the above-described aspects, when the dry gas stream contacts condensed humidifying agent present in discharge line 490, the condensed humidifying agent will be vaporized and carried with the gas stream through an expiratory limb 495. Alternatively, if the dry gas picks up a sufficient amount of condensed humidifying agent to sufficiently humidify the dry gas, the gas may be delivered to the patient instead of being exhausted.

The humidifying system of FIG. 4 may include a controller 460 and sensors 480, 482, 484, 486 may be implemented in a similar manner as in the aspect of FIG. 3 in order to detect relevant system parameters and control the flow of gas and humidifying agent in an optimal manner. Sensor 480 may be implemented to detect temperature and flow rate of the gas being delivered from the gas source 110, sensor 482 may be implemented to detect flow rate, temperature, and pressure of the humidifying agent being delivered to droplet generating device, sensor 484 may be implemented to detect the level of humidifying agent, sensor 486 may be implemented to detect the temperature of the heating element 420, and sensor 488 may be implemented to detect the gas flow rate, gas temperature, relative humidity, and absolute humidity in the discharge line 490. As illustrated in FIG. 4, the controller 460 is coupled to receive information and control one or more of the gas source 110, the pump 440, the droplet generating device 470, and the heated element 420. The controller 460 may use some or all of the data detected from the various sensors to provide optimal control of any of the controllable parameters such as volume, rate of gas being delivered from the gas source, flow rate of humidifying agent to the droplet generating device 470, rate of operation of the droplet generating device 470, and temperature of the heated element 486. Furthermore, as discussed above, because the delivery of humidifying agent is decoupled from the heating element 420 (i.e. the heating element heats the gas/humidifying agent independently of the delivery of the humidifying agent), the controller 460 has more flexibility as to when to heat and when to deliver humidifying agent.

The above-described aspects are directed to pulsing the delivery of humidifying agent in order to reduce condensation present in a discharge line 365, 490. As described above, the pulsing method can be used in each of the exemplary aspects illustrated in FIGS. 2 to 4. However, the aspects illustrated in FIGS. 3 and 4 also provide a method of delivering humidified gas to a patient 140. The method is carried out essentially in the same manner as described above, except that rather than removing condensation from the discharge line 365, 490 by pulsing, the method provides a precise manner of delivering humidified gas to a patient while avoiding the disadvantages of a stationary water humidifier. The elements of the method that are the same as described above are therefore omitted. More specifically, the method of delivery uses the controller 360, 460 of FIGS. 3 and 4 to optimize the delivery of humidifying agent to the gas inlet line 390, 430 separately from pulsing the gas flow.

The method of delivering humidified gas is the same as the method described above with respect to the pulsing method, except that the pulsing step is omitted. That is, the apparatus of FIGS. 3 and 4 are operated by the controller 360, 460 to control the delivery of humidifying agent, among the other controllable parameters discussed above, to deliver an optimized humidified gas. Thus, rather than sharply reducing the amount of humidifying agent delivered to a volume of gas in order reduce condensation, the method of delivering humidifying agent includes flowing humidifying agent at a controlled flow rate to the humidifier portion 300, 400 via a humidifying agent input line 350, 450. The delivery of humidifying agent is further optimized by using one or more of the sensors 380, 382, 384, 386, 480, 482, 484, 486, 488. The sensors detect the same parameters discussed above. The parameters are inputted to the controller 360, 460, and the controller 360, 460 then adjusts the controllable variables discussed above to deliver a precisely controlled amount of humidifying agent to a volume of gas while avoiding the problems of a stationary water humidifier. As discussed above, in the aspect of FIG. 4, one of the controllable variables may also be the rate of actuation of the droplet generating device 470.

It is within the scope of the invention that any of the above aspects can be duplicated within the same humidifying system 100 to provide multiple points of entry to introduce humidifying agent to the respiratory circuit 120. This is especially true with the aspect of FIG. 4 because the production of fine droplets generally requires a low flow rate. Thus, for enough humidifying agent to be delivered to fully humidify the volume of gas traveling through the respiratory circuit 120, several humidifying portions 400 may be implemented in a single humidifying system 100. In such systems, the controller 460 may be used to synchronize and optimize the delivery of humidifying agent.

While aspects of the present invention have been described in a discrete manner to facilitate understanding, it is within the scope of the invention that the aspects may be used in conjunction with each other. For example, the humidifying portions 200, 300, 400 illustrated in FIGS. 2-4 may all be present in a single humidification system 100. Additionally, while the diverter 220 is illustrated only in FIG. 2, it is within the scope of the invention that the diverter 220 may be used in conjunction with the aspects of FIGS. 3 and 4. In such a case, the controller 250, 360, 460 would control the diverter 220 in addition to controlling the other features.

Furthermore, it is within the scope of the invention that a humidification system 100 may include multiple humidifying portions 200, 300, 400 of the various types disclosed above. Additionally, the methods disclosed above may all be used within the same humidification system 100. For example, in the aspects of FIGS. 3 and 4, the method of pulsing may be used if condensation occurs in the discharge line 365, 490, while the method of delivering humidifying agent may be implemented during all other times.

The invention has been described herein with reference to various specific and preferred materials, embodiments and techniques. It should be understood that many modifications and variations to such materials, embodiments and techniques will be apparent to those skilled in the art within the spirit and scope of the invention. Therefore, the invention should not be limited by the above description, and to ascertain the full scope of the invention, the following embodiments should be referenced.

All references cited herein are hereby incorporated by reference in their entirety.

The invention claimed is:

1. A method of reducing condensed humidifying agent in a humidification system, the method comprising:
   providing a humidification system comprising a respiratory circuit for delivering a volume of gas to a patient and a humidifier portion for delivering a humidifying agent to the volume of gas;
   pulsing a delivery of humidifying agent to the volume of gas at a pulsed interval via the humidifier portion, the pulsing interval commencing immediately after patient exhalation or during patient inhalation;
   heating the volume of gas upstream of a discharge line of the respiratory circuit; and
   vaporizing, during a non-pulsed interval, condensed humidifying agent present in the discharge line to reduce the condensed humidifying agent present in the humidification system, the non-pulsed interval commencing immediately after patient inhalation or during patient exhalation,
   wherein the vaporizing step includes passing the heated volume of gas through the discharge line.

2. The method of claim 1, wherein the humidifying agent comprises water.

3. The method of claim 1, wherein the pulsing step comprises actuating a diverter to at least partially direct the volume of gas toward the humidifier portion.

4. The method of claim 1, wherein the vaporizing step comprises actuating a diverter to at least partially direct the volume of gas away from the humidifier portion.

5. The method of claim 1, wherein the pulsing step comprises actuating a diverter to direct all of the volume of gas toward the humidifier portion.

6. The method of claim 1, wherein the vaporizing step comprises actuating a diverter to direct all of the volume of gas away from the humidifier portion.

7. The method of claim 1, wherein the pulsing step further comprises increasing an amount of the humidifying agent delivered to the volume of gas relative to an amount of humidifying agent delivered to the volume of gas during the non-pulsed interval.

8. The method of claim 1, wherein the pulsing step further comprises providing a greater flow of humidifying agent to the humidifier portion than a flow of humidifying agent provided to the humidifier portion during the non-pulsed interval.

9. The method of claim 8, wherein no amount of humidifying agent is delivered to the humidifier portion during the non-pulse interval.

10. The method of claim 1, wherein the pulsing step further comprises placing a heated element in contact with a flow of humidifying agent.

11. The method of claim 10, wherein the heated element comprises a porous thermally conductive material.

12. The method of claim 1, wherein the pulsing step further comprises producing humidifying agent droplets via an ultrasonic droplet generator and vaporizing the humidifying agent droplets via a heated element.

13. The method of claim 1, wherein the vaporizing step further comprises placing the heated volume of gas in contact with the condensed humidifying agent.

14. The method of claim 11, wherein the thermally conductive material comprises a fiber wool or sintered particulate mass.

15. The method of claim 1, wherein the condensed humidifying agent is formed prior to the non-pulsed interval.

16. The method of claim 1, further comprising timing the pulsing based on one or more parameters detected by one or more sensors other than relative humidity or absolute humidity.

* * * * *